United States Patent [19]

Peters et al.

[11] Patent Number: 5,070,018
[45] Date of Patent: Dec. 3, 1991

[54] METHOD OF CONTROLLING GENE EXPRESSION

[75] Inventors: Norman K. Peters, Berkeley; John W. Frost, Menlo Park; Sharon R. Long, Palo Alto, all of Calif.

[73] Assignee: The Board of Trustees of the Leland Stanford Junior University Stanford, Calif.

[21] Appl. No.: 928,796

[22] Filed: Nov. 7, 1986

[51] Int. Cl.$^5$ ............ C12N 15/00; C12N 1/20; C12P 21/00
[52] U.S. Cl. ............ 435/172.3; 435/70.1; 435/71.1; 435/183; 435/252.2; 435/252.3; 435/320.1; 435/878; 935/35; 935/41; 935/43
[58] Field of Search ............ 435/183, 320, 172.3, 435/252.2, 878, 70.1, 71.1; 935/35, 41, 43

[56] References Cited

PUBLICATIONS

Firmin, J. L. et al., 1986 (6 Nov.) Nature 324:90-92.
Peters, N. K. et al., 1986 (29 Aug.) Science 233:977-980.
Redmond et al., 1986 (16 Oct.) Nature 323:632-635.
Robinson, Trevor, 1983, The Organic Constituents of Plants, Cordus Press, p. 201.
Olson et al., 1985, Bio/Technology 3:143-149.

*Primary Examiner*—Elizabeth C. Weimar
*Assistant Examiner*—P. Rhodes
*Attorney, Agent, or Firm*—Bertram I. Rowland; Richard L. Neeley

[57] ABSTRACT

A method of controlling expression of a DNA segment under the control of a nod gene promoter which comprises administering to a host containing a nod gene promoter an amount sufficient to control expression of the DNA segment of a compound of the formula:

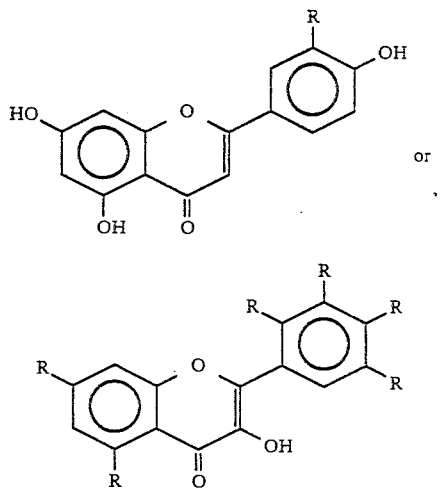

in which each R is independently H or OH, is described.

12 Claims, No Drawings

METHOD OF CONTROLLING GENE EXPRESSION

The Federal Government has rights in this invention as a result of partial support of the work described herein by the National Institutes of Health and the Department of Energy.

BACKGROUND OF THE INVENTION

1. Field of the Invention

This invention relates generally to control of gene expression and more particularly to induction and inhibition of the nod genes from *Rhizobium meliloti*.

2. Description of the Background

The ability to isolate and manipulate nucleic acid sequences encoding polypeptides has greatly increased research efforts into improved means for expressing these proteins in both natural and foreign hosts. Due to their ready availability, easy manipulation, and economy of use, unicellular microorganisms (e.g., bacteria and yeast) have been studied and utilized extensively for the production of such polypeptides.

When employing unicellular organisms, it is desirable to enhance the production of the polypeptide product of interest, with minimal interference in the production of other materials necessary for the cell's growth and/or maintenance. This permits maximal production of the desired products over an extended time period, with concomitant cost benefits. For these and other reasons, methods have been devised for selectively enhancing polypeptide expression in bacterial hosts.

One technique has been to couple the gene of interest to a promoter that is recognized by the host and allows for controlled regulation of efficient transcription of the gene encoding the polypeptide. Frequently, a "high-producing" host promoter is used, i.e., one associated with the natural production of a polypeptide that normally comprises a high percentage of the total protein of the host (or at least a promoter that provides a high transcription rate). Typically, inducible promoters are preferred, because they permit coupled expression of the gene in the presence of an inducing agent.

Generally, inducible promoters are useful only to the extent that the regulatory circuit and its components are understood and further to the extent that the components do not cross-react with other promoter or repressor systems. Thus, well-defined and highly specific regulatory circuits, particularly promoter and regulatory components, have significant utilities.

In parallel to the above, the expanding research base concerning plant and related bacterial physiology has resulted in the development of various new agents active in plant nutrition, growth and protection (e.g., pesticides, growth regulators, including hormones, and herbicides). Presently, such new agents (as well as those previously developed) are usually applied by spraying or irrigating the materials on most, if not all, of the field where the crops are grown. Frequently, as the agent need only interact with a certain portion of the plant (e.g., the roots) to be effective, this bulk application results in substantial waste. Also, in some cases, bulk application can actually prove to be harmful, when, for example, pesticide levels surpass safe limits.

The ability of certain bacteria in the gram-negative group Rhizobium to infect and form nodules on the roots of plants has provided a new potential avenue for selectively introducing agents into plants. The bacteria invade the roots, multiply and eventually inhabit cells of the nodules as intracellular symbionts. This invasion capability for Rhizobium essentially extends through one family of plants, the Leguminosae, which includes such important crops as soybean, alfalfa, clover, beans, garden peas, peanuts, cowpeas, etc. However, to effectively utilize this capability for introducing additional desired agents requires increased understanding of the genetics of nodulation and of the inducers that control expression of the nodulation genes.

Thus, there exists a significant need for additional and improved means for applying agents to crops and other plants of interest. Further, there exists a significant need for the development of defined and specific inducible promoter systems for use in bacteria, such as those capable of forming root nodules. The present invention fulfills these needs.

DESCRIPTION OF THE RELEVANT LITERATURE

Nodulation (nod) genes, which certain bacteria require for invasion and stimulation of nodule formation on plants, have been identified in and cloned from several Rhizobium species. Long, S. et al., (1982) Nature 298:485–488; Hombrecher, G. et al., (1983) EMBO J. 2:947–952; Schofield, P. et al., (1983) Mol. Gen. Genet. 192:459–465; and Kondorosi, E. et al., (1984) Mol. Gen. Genet. 193:445–452. The host specificity of the nodulation genes of various Rhizobium species is known, but a number of nod mutants are subject to inter-species complementation. Dusha, I. et al., (1981) Mol. Gen. Genet. 184:318–325; Fisher, R. et al., (1985) Appl. Env. Microbiol. 49:1432–1435; and Djordjevic, M. et al., (1985) Plant Mol. Biol. 4:147–160. It has been reported that certain bacterial characteristics are altered by exposure to plants or plant exudates. See, Dazzo, F. and Hubbell, D. (1982) in *Nitrogen Fixation* 2, ed. Broughten, W. (Oxford University Press), pp. 275–309; Vincent, J. (1974) in *Biology of Nitrogen Fixation* ed. Quispel, A. (North-Holland Press, Amsterdam), pp 265–341; and Bhagwat, A. and Thomas, J. (1982) Appl. Env. Microbiol. 43:800–805. Also, an *E. coli* regulatory system has been described in which a regulatory gene is transcribed divergently from the gene set it regulates. Lee, N. et al., (1981) Proc. Natl. Acad. Sci. U.S.A. 78:752–756.

Additionally, this application is related to U.S. patent application Ser. No. 788,911, filed Oct. 18, 1985, entitled: "Bacterial Promoters Inducible by Plant Extracts" to Sharon Long et al. The earlier patent application describes promoters that can be induced according to the method of the present invention.

SUMMARY OF THE INVENTION

The present invention relates to a method of inducing expression of a structural or other protein-encoding gene or a DNA segment not coding for protein production that is under the control of an inducible bacterial nod gene. In carrying out the method, a host containing a nod gene promoter is administered with an amount of luteolin, apigenin, or derivative thereof as defined herein sufficient to activate expression of the gene or DNA segment. Inhibitors have also been identified. Thus, it is possible to activate or inhibit expression of nod genes in an easily controllable manner.

DESCRIPTION OF THE PREFERRED EMBODIMENTS

In accordance with the present invention, a method is provided for controlling expression of the inducible nod genes of the alfalfa symbiont *R. meliloti*. Induction is controlled by certain flavone compounds, the most active of which (as an inducer) is luteolin, whose formula is shown below as Formula Ia. Apigenin is also active as an inducer although at lower specific activity and is closely related in structure as shown below in Formula Ib. Compounds in which R of Formula I is either H or OH are thus both active inducers.

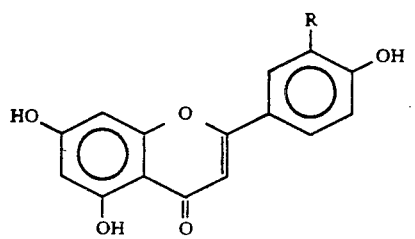

R = H or OH
a:R = OH
b:R = H

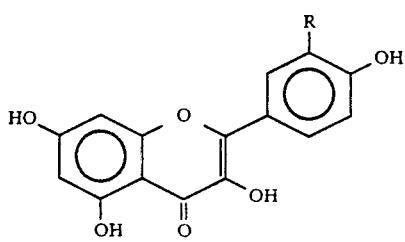

R = H or OH
a:R = OH

Compounds having the structure shown in Formula II are inhibitors of inducible nod promoters. Quercetin, which has the structure shown in Formula IIa, has been experimentally demonstrated to act as a competitive inhibitor of luteolin in a biological assay for gene induction. In fact, all compounds tested to date having a 3-OH group (i.e., all flavonols) have acted as inhibitors of gene expression controlled by inducible nod promoters.

The flavones and flavonols of the present invention are readily available compounds that can be purchased from commercial sources or produced by synthetic techniques. Luteolin, apigenin and quercetin are all commercially available. The Baker-Venkataraman rearrangement reaction of 2-aroyloxyacetophenones to 2-hydroxy derivatives of dibenzoylmethanes followed by cyclization by, e.g., hydrogen bromide in glacial acetic acid readily produces flavones whose substitution patterns can be readily predetermined by the substitution pattern of the original phenyl groups. An example of such a synthesis is set forth in Cramer and Elsching, *Chem. Ber.* (1956) 89:8. Also see Hilgetag and Martini, eds., *Preparative Organic Chemistry*, Wiley-Interscience, New York (1972), page 1071.

An induction assay has been used to demonstrate structure-activity relationships. Induction assays of nodABC-lacZ using compounds related in structure to luteolin suggest structural features of the B and C rings that are required for inducing activity. The inactivity of chrysin demonstrates the necessity for hydroxylation at the 3' and/or 4' positions of the B-ring. Activity of apigenin shows that a hydroxylated 4' position confers partial function and that 3' hydroxylation is required for full activity. Failure of morin and quercetin to induce demonstrates that hydroxylation at the 2' position or the 3 position renders the molecule ineffective as an inducer. However, compounds hydroxylated at the 3 position are effective as inhibitors. The structures of these compounds and others tested are identified below. Only luteolin and apigenin showed induction activity when measured by the assay procedures described herein.

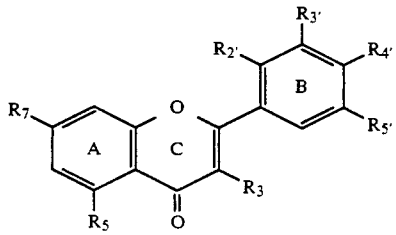

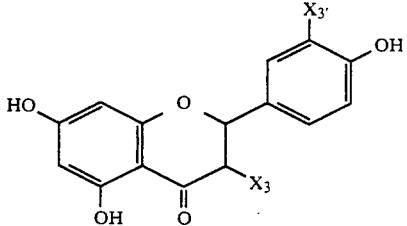

flavone (III) $R_{2'} = R_{3'} = R_3 = R_{4'} = R_{5'} = R_5 = R_7 = H$;
flavanol (III) $R_{2'} = R_{3'} = R_{4'} = R_{5'} = R_5 = R_7 = H, R_3 = OH$;
chrysin (III) $R_{2'} = R_{3'} = R_3 = R_{4'} = R_{5'} = H, R_5 = R_7 = OH$;
fisetin (III) $R_{2'} = R_{5'} = R_5 = H, R_{3'} = R_3 = R_{4'} = R_7 = OH$;
morin (III) $R_{3'} = R_{5'} = H, R_3 = R_{2'} = R_{4'} = R_5 = R_7 = OH$;
myricetin (III) $R_{2'} = H, R_{3'} = R_3 = R_{4'} = R_{5'} = R_5 = R_7 = OH$;
quercetin (III) $R_{2'} = R_{5'} = H, R_{3'} = R_3 = R_{4'} = R_5 = R_7 = OH$;
apigenin (III) $R_{2'} = R_{3'} = R_3 = R_{5'} = H, R_{4'} = R_5 = R_7 = OH$;
dihydroquercetin (IV) $X_3 = X_{3'} = OH$;
maringenin (IV) $X_3 = X_{3'} = H$;

The concentration dependence of nodABC-lacZ induction by luteolin resembles that observed for other inducible systems such as the lactose operon and the arabinose operon; however, full induction of nodABC operon occurs at inducer concentrations three to five orders of magnitude lower than the inducers of the metabolic lactose and arabinose operons. These inducer systems are described in detail in Sadler and Novick, (1965) *J. Mol. Biol.* 12:305 and Doyle et al., (1972) *J. Bacteriol.* 110:56.

The inducer molecules reported here can be utilized in study of the nodABC gene activation mechanism. Induction of nodABC requires not only the plant inducer, but also the gene product of nodD, as described in U.S. patent application Ser. No. 788,911, identified above. Synthesis of radiolabeled inducer will make it possible to study the interaction of luteolin with the nodD gene product or other possible receptor molecules, and to follow the fate of luteolin in the bacterium. Other uses are set forth below.

*R. meliloti* successfully forms nodules on a few genera of legumes, including Medicago (alfalfa), Melilotus (sweet clover), and Trigonella (fenugreek). Leguminous plants, such as beans, soybeans, peanuts, cowpeas, clover, lentils, and garden peas, outside the R. meliloti cross-inoculation group also yield exudates which activate R. meliloti nodABC. Since nodD gene product is required for induction and can complement across species, flavone and flavonol or similar compounds as described in this specification should act as inducers or inhibitors for other legume/Rhizobium symbiotic pairs.

When a regulatory DNA segment of the type described in U.S. patent application Ser. No. 788,911 is fused to a structural gene or other DNA segment of interest and then ligated to an extrachromosomal element, which in turn is introduced into a bacterium, the bacterium can be introduced into locus (e.g., a field) that has been or will be planted in legumes. Normally such a bacterium would become associated with the roots of plants and would then produce the gene product in the presence of plant exudate containing luteolin. As a result of the present invention, it is possible to control expression of the bacterial product by preparing an inoculant containing a compound of the invention in order to activate transcriptional initiation of the structural gene at a higher rate than normal. It is also possible to aid nodulation using unmodified R. meliloti by using an inoculation containing this bacterium and an inducer described in this specification.

Flavone and flavonol compounds of the invention are transported by a plant and thus readily reach the unicellular microorganisms (bacteria) living symbiotically in the plants when applied to the plant, including plant parts such as leaves or roots. Compounds can also be applied directly to seeds in the presence of or prior to application of bacteria. Such compounds are generally present in the form of a composition containing an inert, biologically acceptable carrier. Such carriers, especially for use in compositions intended for agricultural purposes, are well known. Typical carriers include organically acceptable oils, surfactants, aqueous or organic solvents and solutions, and solid carriers (such as talc, peanut hulls, clays, dusts and the like). The compositions contain from 0.1 to 95% active ingredients with the remainder being inert or a compound having a different utility (e.g., a pesticide or herbicide). Compositions containing from 1 to 60% active ingredients are preferred.

Thus, bacteria can be induced to assist plants to exhibit resistance against invasion by foreign organisms, such as pathogens, nematodes, insects, and the like, by providing polypeptides that act either alone or with their products or other agents as toxins against such pests (e.g., Bacillus thuringiensis endotoxin protein). These agents may also protect against chemical imbalances or excess toxic chemicals, and the like. The agents can control amino acid levels in the plants, and generally increase or decrease nutrient levels. Further, the bacteria can contain genes encoding agents having growth control activity over the plants or portions thereof (e.g., seeds, roots, shoots, leaves and fruit). Indeed, selective herbicidal proteins or proteins useful in herbicide detoxification (such as against residual atrazine) could also be produced.

Genes encoding polypeptides capable of inducing herbicidal resistance in plants have previously been cloned and introduced into plants. These include the bacterial genes encoding chlorsulfuron and sulfmeturon resistance, as well as the glyphosate resistance gene from Salmonella. If desired, these and various additional genes may be provided in a polycistronic form.

The particular structural gene or DNA segment inserted as a plant modifying agent is not critical to this aspect of the present invention, and any polypeptide, protein, or other compound of interest may be prepared employing these constructions as described herein.

Specific techniques for introducing structural genes into bacteria in order that the structural genes will be expressed in bacterial living symbiotically in the plant host are set forth in U.S. patent application Ser. No. 788,911, identified above.

Using the induction method of the present invention, it is also possible to construct novel bacterial strains that produce proteins or polypeptides without requiring contact with plants or their exudates. By transforming bacteria with DNA segments containing the structural nodD gene and the regulatory region for the nodABC operon fused to DNA sequences from various sources, the bacteria can, at appropriate times, express polypeptides without requiring the presence of a plant, a possibility that did not exist prior to identification of the inducers.

In another embodiment of the invention, genes coding for the synthesis of luteolin can be introduced into a bacterium containing or modified to contain nod genes so that luteolin is expressed within the bacterium, thus activating expression of the inducible nod genes. The genes coding for the synthesis of luteolin can, if desired, be placed under the control of a second promotor, such as the lac promotor. This should allow nodulation to occur in plants that do not contain luteolin or another nod gene inducer.

Inhibitors of the invention can be utilized to control growth of wild-type Rhizobium species and/or inhibit expression of nodulation or other phenotypes resulting from expression of DNA under the control of inducible nod promoters. For example, nodulation by wild-type Rhizobium species can be controlled in a field or other plant-growth locus by administration of quercetin or another flavonol. Plant seed inoculated with a desirable Rhizobium species and an excess of luteolin (for example) can then be planted in the same locus. Such a procedure will avoid problems of the type previously encountered when seed is inoculated with a Rhizobium species. In the past, competition from wild-type species has reduced the effectiveness of inoculation. Inhibitors can also be used in cultures of nod-promoter containing microorganisms (described above) to counteract and control the expression of nod gene products.

Compounds that will hydrolyze or otherwise react under biological conditions to produce compounds of the invention are considered equivalent thereto since administration of such compounds is equivalent to administration of the specific compounds indicated. Typical of such compounds are esters and ethers of the hydroxyl groups shown, especially lower alkanoyl (such as $C_1$-$C_4$) esters and lower alkyl (such as $C_1$-$C_4$) ethers. Acetate esters and methyl ethers are especially common and can be utilized to produce long-acting compositions as a result of release of the indicated compounds under biological conditions (e.g., in the presence of deacetylation enzymes).

The following examples are offered by way of illustration and not by way of limitation.

EXAMPLES

Purification of the Inducer

The inducer was monitored during purification by assaying induction of a nodABC-lacZ translational fusion borne on plasmid pRmM57 (J. T. Mulligan and S. R. Long, *Proc. Natl. Acad. Sci. U.S.A.* (1985) 82:6609). Preliminary tests of alfalfa seed exudate indicated that the inducer molecule was probably a small aromatic compound. Activity of the plant exudate was not affected by treatment with heat, proteases, or nucleases. However, activity was removed from exudates by treatment with activated charcoal or by dialysis through membranes with a molecular weight exclusion limit of 2,000 kd.

The exudate from alfalfa seeds was fractionated by high pressure liquid chromatography (HPLC) using a reverse phase $C_{18}$ column. Fractions were assayed for nodABC-lacZ inducing activity. Activity eluted as a broad peak between 95 and 100 percent methanol, indicating that the inducing molecule had significant hydrophobic character. The inducer molecule was partially purified by extracting the inducing factor into diethyl ether. These ether-extracted compounds were separated by HPLC, and fractions containing the inducing activity again eluted along with several ultraviolet (UV) absorbing compounds between 95 and 100 percent methanol. To resolve the inducer molecule from these co-eluting compounds, the ether-extracted materials were fractionated on a 50–100% methanol:water gradient. Under these conditions, the various components were resolved, and the majority of inducing activity correlated with a single absorbance peak eluting at 90–95% methanol. Other UV absorbing compounds with little inducing activity eluted between 70 and 75 percent methanol. Fractions containing the most activity (90–95% methanol) were pooled for structural analysis.

Identification of the Inducer Molecule

The UV and visible absorbance spectra of the yellow colored inducer were determined in methanol and methanol/NaOH. As listed in Table I below, the Band I absorbance of the inducer as measured in methanol displayed a bathochromic shift of 50 nm when strong base was added. The inducer spectra were compared to spectra of various classes of molecules including flavonoids. The observed absorption maxima and the magnitudes of the bathochromic shifts in strong base are characteristic of flavonoid molecules, particularly flavones. Further spectral analysis of the unknown compound in weak base and when complexed with a metal is consistant with the reported spectra of 3', 4', 5, 7-tetrahydroxyflavone (luteolin; Table I), a compound which had previously been extracted from alfalfa seeds. Synthetic luteolin was found to have spectra indistinguishable from that of the purified inducer molecule.

TABLE I

| | Absorbance maxima in nm | | | |
|---|---|---|---|---|
| | Band I | | Band II | |
| Solvent | luteolin | inducer | luteolin | inducer |
| MeOH | 349 | 351 | 253,267 | 256,267 |
| MeOH/NaOH | 401 | 405 | 266 | 266 |
| MeOH/AlCl$_3$ | 328,426 | 328,426 | 271 | 271 |
| MeOH/AlCl$_3$/HCl | 355 | 357 | 274 | 275 |
| MeOH/NaOAc | 384 | 384 | 269 | 269 |
| MeOH/NaOAc/H$_3$BO$_3$ | 370 | 372 | 259 | 259 |

Spectral analyses were performed as described in and data for luteolin were obtained from Mabry et al., (1970) "The Systematic Identification of Flavonoids", Springer-Verlag, New York.

Isolated inducer and synthetic luteolin were analyzed using mass spectrometry and nuclear magnetic resonance spectroscopy (NMR). Both synthetic luteolin and isolated inducer share a molecular ion $M^+$ m/e=286 and a base peak m/e=153. The proton ($^1$H) NMR of isolated inducer is identical to synthetic luteolin. Thus isolated inducer and synthetic luteolin have indistinguishable absorption spectra, mass spectra and proton NMR.

Inducer Activity

To test the biological activity of luteolin, its ability to induce nodABC-lacZ was compared with that of purified inducer at concentrations ranging over six orders of magnitude. The concentration dependence of the induction by the two compounds is indistinguishable. Therefore, synthetic luteolin displays the same biological activity as the isolated inducer.

Compounds similar in structure to luteolin were tested for their ability to induce nodABC-lacZ. The compounds tested are described earlier in this specification. Of the compounds tested, only luteolin and apigenin have detectable inducing activity in the assay used. At 50 μM, which is 100 times the concentration of luteolin required for full induction, apigenin has only 20% the activity of luteolin.

All publications and patent applications mentioned in this specification are indicative of the level of skill of those in the art to which this invention pertains. All such publications and patent applications are herein incorporated by reference in the location cited equally as if each individual publication or patent application had been indicated to be individually incorporated by reference.

Although the invention has been described in some detail by way of illustration and example, it will also be apparent that various changes and modifications can be made without departing from the scope or spirit of the appended claims.

What is claimed is:

1. A method of inducing expression of a DNA segment under the control of an *R. Meliloti* nod ABC gene promoter, which comprises:

administering to a host containing said nod gene promoter an amount sufficient to activate expression of said DNA segment of a compound of the formula:

[Structure: flavone with R at 3' position, OH at 4', HO at 7, OH at 5, carbonyl at 4]

wherein R is H or OH, wherein said administering occurs in the presence of an *R. Meliloti* nod D gene product.

2. The method of claim 1, wherein R is OH.

3. The method of claim 1, wherein said host is *R. meliloti*.

4. The method of claim 1, wherein said host is a unicellular organism genetically engineered to contain said DNA segment.

5. The method of claim 4, wherein said DNA segment is a structural gene.

6. The method of claim 5, wherein said gene encodes a protein conferring pesticidal activity.

7. The method of claim 5, wherein said gene encodes *Bacillus thuringiersis* endotoxin.

8. The method of claim 5, wherein said gene encodes an enzyme conferring resistance to a herbicide.

9. The method of claim 7, wherein said amount produces a concentration in the environment in contact with said host of 0.05 to 5.0 $\mu$M.

10. The method of claim 9, wherein said concentration is about 0.5 $\mu$M.

11. A method of inhibiting production of a DNA segment under the control of an *R. Meliloti* nod ABC gene promoter, which comprises:

administering to a host containing said nod gene promoter an amount sufficient to inhibit expression of said DNA segment of a compound of the formula:

[Structure: flavonol-type with R substituents at multiple positions, OH group, carbonyl]

wherein each R independently is H or OH, wherein said administering occurs in the presence of an *R. Meliloti* nod D gene product.

12. The method of claim 11, wherein said compound is quercetin.

* * * * *